United States Patent
Wong et al.

(10) Patent No.: US 10,945,701 B2
(45) Date of Patent: Mar. 16, 2021

(54) SEGMENT-BASED FLASH SUPPRESSION IN ULTRASOUND COLOR FLOW

(71) Applicant: Siemens Medical Solutions USA, Inc., Malvern, PA (US)

(72) Inventors: King Yuen Wong, Issaquah, WA (US); Chi Hyung Seo, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1084 days.

(21) Appl. No.: 14/473,923

(22) Filed: Aug. 29, 2014

(65) Prior Publication Data

US 2016/0058425 A1    Mar. 3, 2016

(51) Int. Cl.
*A61B 8/06* (2006.01)
*A61B 8/08* (2006.01)
*G06T 5/00* (2006.01)
*G06T 7/215* (2017.01)

(52) U.S. Cl.
CPC ............. *A61B 8/06* (2013.01); *A61B 8/5276* (2013.01); *G06T 5/005* (2013.01); *G06T 7/215* (2017.01); *A61B 8/488* (2013.01); *A61B 8/5207* (2013.01); *G06T 2207/10132* (2013.01); *G06T 2207/30104* (2013.01)

(58) Field of Classification Search
None
See application file for complete search history.

(56) References Cited

U.S. PATENT DOCUMENTS

| | | | | |
|---|---|---|---|---|
| 5,152,292 A | * | 10/1992 | Karp | G01S 15/8981 600/443 |
| 5,740,266 A | * | 4/1998 | Weiss | G06T 5/30 382/128 |
| 5,782,769 A | | 7/1998 | Hwang et al. | |
| 6,217,520 B1 | * | 4/2001 | He | A61B 8/00 600/467 |
| 6,287,258 B1 | | 9/2001 | Phillips | |
| 6,760,486 B1 | * | 7/2004 | Chiao | G01S 7/52046 382/128 |
| 9,451,932 B2 | * | 9/2016 | Zwirn | A61B 8/4488 |
| 2003/0236460 A1 | * | 12/2003 | Ma | A61B 8/06 600/441 |
| 2006/0184021 A1 | * | 8/2006 | Kim | G06K 9/40 600/437 |
| 2008/0097212 A1 | * | 4/2008 | Srinivasan | A61B 8/06 600/453 |
| 2009/0024033 A1 | * | 1/2009 | Murashita | A61B 8/06 600/443 |
| 2009/0306503 A1 | * | 12/2009 | Srinivasan | A61B 8/00 600/441 |
| 2009/0306513 A1 | * | 12/2009 | Srinivasan | A61B 8/06 600/454 |
| 2010/0266099 A1 | * | 10/2010 | Busch | A61N 5/1048 378/65 |
| 2010/0331701 A1 | * | 12/2010 | Hamada | A61B 8/06 600/454 |
| 2011/0208056 A1 | * | 8/2011 | Datta | A61B 8/06 600/441 |

* cited by examiner

*Primary Examiner* — Rochelle D Turchen

(57) ABSTRACT

Flash suppression is provided in motion imaging. Separate regions of motion in a same frame or image are tested for flash independently. The size, shape, spatial variance, and/or location of a given region are used to categorize a level or likelihood of flash artifact for that region. Based on the level or likelihood, the motion information is altered to reduce flash.

17 Claims, 4 Drawing Sheets

SEGMENT-BASED FLASH SUPPRESSION IN ULTRASOUND COLOR FLOW

BACKGROUND

This present embodiments relate to motion imaging. In particular, flash artifact suppression is provided for imaging flow or tissue motion with color ultrasound imaging.

Flash artifacts arise from decorrelation caused by tissue or probe motion. Because of the underlying physiologic interaction with ultrasound, the flash artifacts often manifest as a large patch of false motion that covers both the tissue and true motion. Flash artifacts from signal decorrelation are usually narrowband and of low velocity. High-pass clutter filtering using Fourier transforms and low velocity thresholding are mostly effective at the expense of low flow sensitivity. However, signal decorrelation caused by reverberations from a nearby beating heart, which may not be in the motion region of interest at all, or certain organ movement, such as bowel movement, often has a broader bandwidth and higher mean velocity. Traditional Fourier-based clutter filters are ineffective for suppressing such flash artifact.

BRIEF SUMMARY

By way of introduction, the preferred embodiments described below include a method, system, computer readable medium, and instructions for flash suppression in motion imaging. Separate regions of motion in a same frame or image are tested for flash independently. The size, shape, spatial variance, and/or location of a given region are used to categorize a level or likelihood of flash artifact for that region. Based on the level or likelihood, the motion information is altered to reduce flash.

In a first aspect, a method is provided for flash suppression in color flow using an ultrasound imaging system. Color flow ultrasound data representing a patient is acquired. The color flow ultrasound data is segmented into one or more contiguous regions of flow. Each of the contiguous regions is unconnected to others of the contiguous regions. Each of the contiguous regions is categorized by size and shape. A flash artifact in the color flow ultrasound data of each of the contiguous regions is suppressed based on the categorization for the respective contiguous region. A color flow image is generated with the color flow ultrasound data after the suppressing. The color flow image represents the patient.

In a second aspect, a non-transitory computer readable storage medium has stored therein data representing instructions executable by a programmed processor for flash artifact suppression in Doppler imaging. The storage medium includes instructions for: scanning a plurality of locations with ultrasound; estimating Doppler values for the locations; identifying the flash artifact as a function of size and shape of a group of spatially connected ones of the locations with Doppler values; altering the Doppler values for the group of spatially connected ones of the locations in response to the identifying of the flash artifact; and generating a Doppler image with the Doppler values, including altered Doppler values resulting from the altering.

In a third aspect, a system is provided for flash suppression in color flow. A transducer and beamformer are for scanning a scan region. A Doppler estimator is configured to estimate motion values representing samples of the scan region at different locations. A processor is configured to identify a flash artifact separately for each of unconnected regions of motion within the scan region and to reduce the motion values by different amounts for the unconnected regions.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Flash artifacts are identified and suppressed by an ultrasound system. For example, color Doppler motion artifacts (e.g., non-slow moving or wide bandwidth) that cannot be removed by traditional Fourier-based clutter filters are suppressed. Segmentation is used to identify regions of flow. The probability of flash artifacts being in each flow region is determined based on the region's size, shape, and/or other characteristic. The suppression strength in each region is a function of the respective probability and local motion statistics. As a result, areas of strong artifact are suppressed more while true flow may be minimally affected.

In one embodiment, a flow image is segmented into connected flow regions. The regions are categorized by physical size and shape using spatial filtering and edge detection. A probability of flash is assigned for each region based on size and shape. Any flash artifacts are removed by reducing their energy and/or velocity. High probability areas are reduced more, and/or high mean velocity and high energy regions are reduced more.

Using segmentation for flash suppression attempts to remove flash artifacts while maintaining blood flow sensitivity. A pre-determined kernel size that would otherwise restrict the size and shape of artifacts that can be removed is not used. The incorrect assumption of flash being impulsive is not relied upon. Moreover, suppression strength is adaptive because the suppression is proportional to the measured flow statistics of the artifacts. Consequently, flash artifacts of various shapes and strength may be substantially removed or subdued while weak blood flow away from flash artifacts may be minimally affected.

Figure 1:
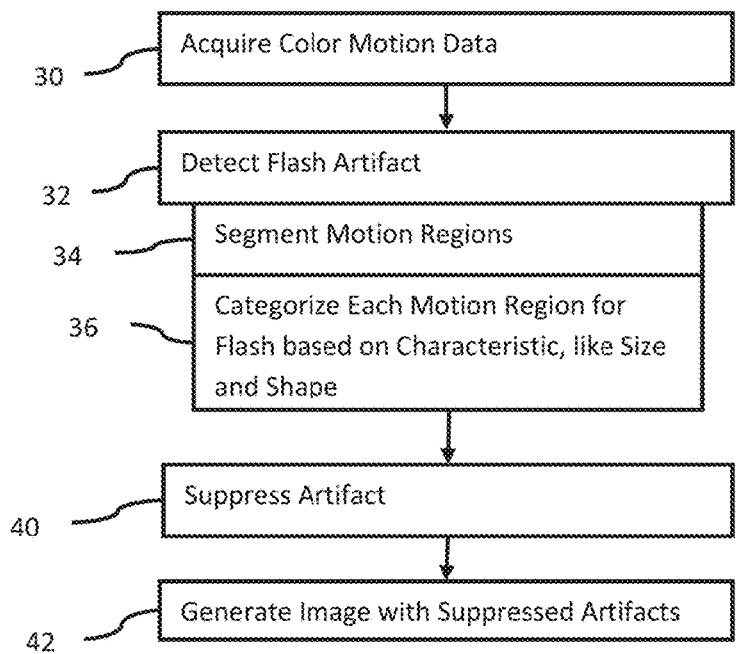
FIG. 1 is a flow chart of one embodiment of a method for flash artifact suppression in motion imaging.
Figure 5:
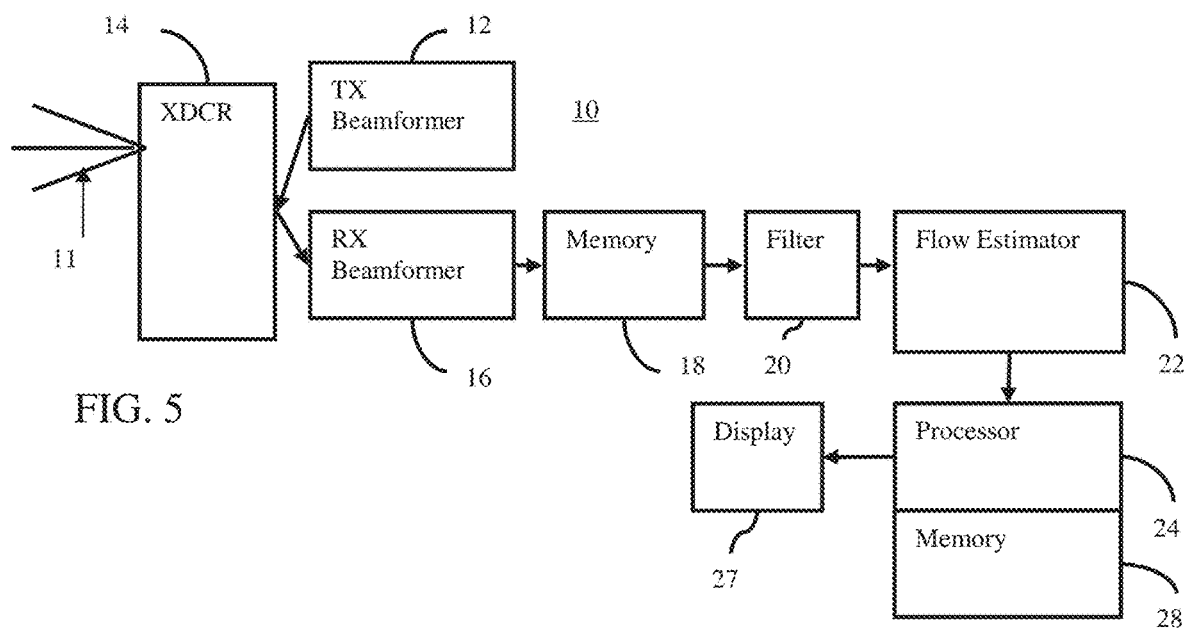
FIG. 5 is a block diagram of one embodiment of a system for flash artifact suppression in motion imaging.

FIG. 1 shows a method for flash suppression in color flow. The method is performed by the ultrasound imaging system 10 of FIG. 5, the processor 24, or a different system, filter, and/or processor. For example, the ultrasound imaging system 10 acquires, segments, categorizes, suppresses and generates an image. As another example, the processor 24 controls acquisition and causes generation of the image by a scan converter, graphics memory, and/or display, but itself segments, categorizes, and suppresses.

The acts of FIG. 1 are performed in the order shown or a different order. Additional, different, or fewer acts than shown in FIG. 1 may be used. For example, an act for calculating a statistical mean or other temporal and/or spatial statistics of the color flow data is provided in order to determine an amount of suppression. In another example, an image is not generated in act 42, and the data with the suppressed artifact is instead stored or used for calculating a value (e.g., average flow velocity).

In act 30, color flow or flow ultrasound data is acquired. Color flow data includes estimates of velocity, energy (e.g., power), and/or variance. In one embodiment, at least velocity is estimated. To estimate the color flow, data representing blood, fluid, or flow of the patient is acquired. In alternative embodiments, tissue motion data is acquired, such as estimates of velocity, energy, and/or variance of tissue motion. Any motion data, whether from flow or tissue movement, may be acquired. Color flow data is used in examples below, but may alternatively or additionally be tissue motion data.

The color flow data is acquired by transfer over a network, loading from memory, and/or by scanning a patient. For transfer or loading, data previously acquired by scanning is acquired. In one embodiment using an ultrasound system, a patient or region is scanned in real-time with the imaging. The scanned region is an interior of an object, such as the patient. The scan is of a volume, plane, or line region. Scanning a plane provides data representing different locations or samples of the plane. The data representing the region is formed from spatial sampling of the object. The spatial samples are for locations distributed in an acoustic sampling grid.

The region for the color flow data scan is a region of interest smaller than a field of view or for the entire field of view. The ultrasound system may scan the field of view using B-mode imaging. The color flow region is a sub-set of that field of view. The user or a processor determines the region of interest in which color flow scanning occurs.

Spatial samples along one or more scan lines are received. Where the transmit beam insonifies just one receive scan line, then samples along that scan line are received. Where the transmit beam insonifies multiple scan lines, then samples along the multiple scan lines are received. To generate the samples for different receive beams, parallel receive beamformation is performed so that the different receive beams are sampled at a same time. For example, a system may be capable of forming two or more, tens or hundreds of receive beams in parallel. Alternatively, signals received from the elements are stored and sequentially processed. Spatial samples are acquired for a plurality of receive lines in the region of interest in response to one and/or in response to sequential transmit beams.

The scanning may be performed a plurality of times to cover the region. The acts are repeated to scan different portions of the region of interest. Alternatively, performing once acquires the data for the entire region of interest.

The complete region of interest is scanned multiple times at different times. Scanning at different times acquires spatial samples associated with flow or motion. Any now known or later developed pulse sequences may be used. A sequence of at least two (flow sample count) transmissions is provided along each scan line. Any pulse repetition frequency, flow sample count, and pulse repetition interval may be used. The echo responses to the transmissions of the sequence are used to estimate velocity, energy (power), and/or variance at a given time. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples may be clutter filtered. The clutter filtering is of signals in the pulse sequence for estimating motion at a given time. A given signal may be used for estimates representing different times, such as associated with a moving window for clutter filtering and estimation. Different filter outputs are used to estimate motion for a location at different times.

Color flow data or tissue motion data is generated from the spatial samples. Any motion data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. "Color" is used to distinguish from spectral Doppler imaging, where the power spectrum for a range gate is estimated. The change in frequency (e.g., Doppler shift) between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time.

The estimation is performed for the different sampled spatial locations. For example, velocities for the different locations in a plane are estimated from echoes responsive to the scanning. Multiple frames of flow data may be acquired to represent the region of interest at different times, respectively.

The estimates may be thresholded. Thresholds are applied to the velocities and/or powers. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

Figure 2:
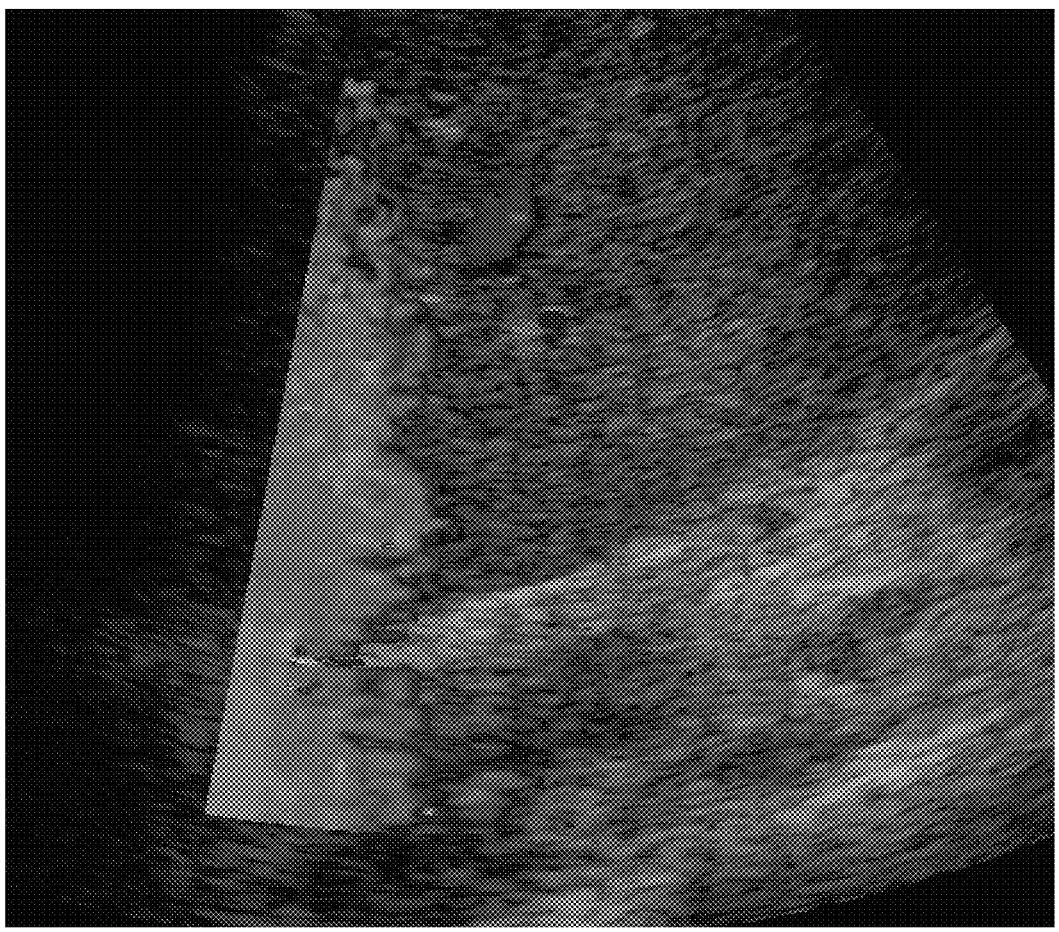
FIG. 2 is an example image with a flash artifact.

The acquired motion data is a frame of data or image representing the patient at a given time, despite being estimated from received signals over a flow sample count. FIG. 2 shows an image generated from a frame of motion data for a given time, at least from the operators perspective. In the example of FIG. 2, the image is generated from color Doppler velocity data. The image is a B-mode image overlaid with or with an incorporated region of interest showing the color Doppler velocities. Within the region of interest, locations with no flow are shown as B-mode data.

A sequence of frames or images may be acquired in real-time or over time. For flash suppression, the detection of flash artifact in act 32 is performed for each frame or image alone without temporal considerations or without reference to frames or images from other times. Alternatively, temporal filtering or aspects are included in detecting the flash artifact. In act 32, the flash artifact is detected using spatial segmentation of act 34 and categorization of act 36. Additional, different, or fewer acts may be provided for detecting in act 32.

In act 34, the color flow ultrasound data is segmented into one or more contiguous regions of flow. The color flow ultrasound date represents a planar or three-dimensional distribution of motion. Some locations in the distribution have no motion or are below the noise threshold for motion. Other locations show motion. In the example of FIG. 2, two larger regions of motion are shown clearly, with the larger of the region having some holes or gaps where no motion occurs. Several smaller regions of motion are shown at the top of the region of interest as well. Other regions exist, but are less noticeable in the black and white reproduction of FIG. 2. For any given location with motion, the location may be connected to or immediately adjacent to another location (e.g., pixel or scan sample location) with motion. These contiguous regions or regions with connected flow not separated by non-flow locations are located by segmentation. The segmentation finds continuous regions of flow locations. If all of the flow locations of FIG. 2 were connected together by other flow locations, then a single contiguous region of flow is found.

Any number of contiguous regions of flow locations is identified. Groupings of connected flow locations that are unconnected with other groupings are identified. In the example of FIG. 2, there are multiple groups of connected flow locations that are unconnected by flow locations with each other. Each group of such locations is segmented as a separate contiguous region. The contiguous regions are unconnected by flow locations to other of the contiguous regions.

Any segmentation may be used. A connected component analysis on a binary map made from whether flow exists at the location or not may be used. A random walker approach may be used. A region growing process may be used. Seed points may be used to find all connected locations.

In one embodiment, the color flow ultrasound data or a binary map of flow locations is low pass spatial filtered. The low pass filtering fills any smaller holes or gaps and may result in fewer contiguous regions. Boundary detection is then applied to the results of the low pass spatial filtering. For example, a gradient process is applied to find edges associated with a gradient between noise and flow. Other boundary detection may be used.

Figure 3:
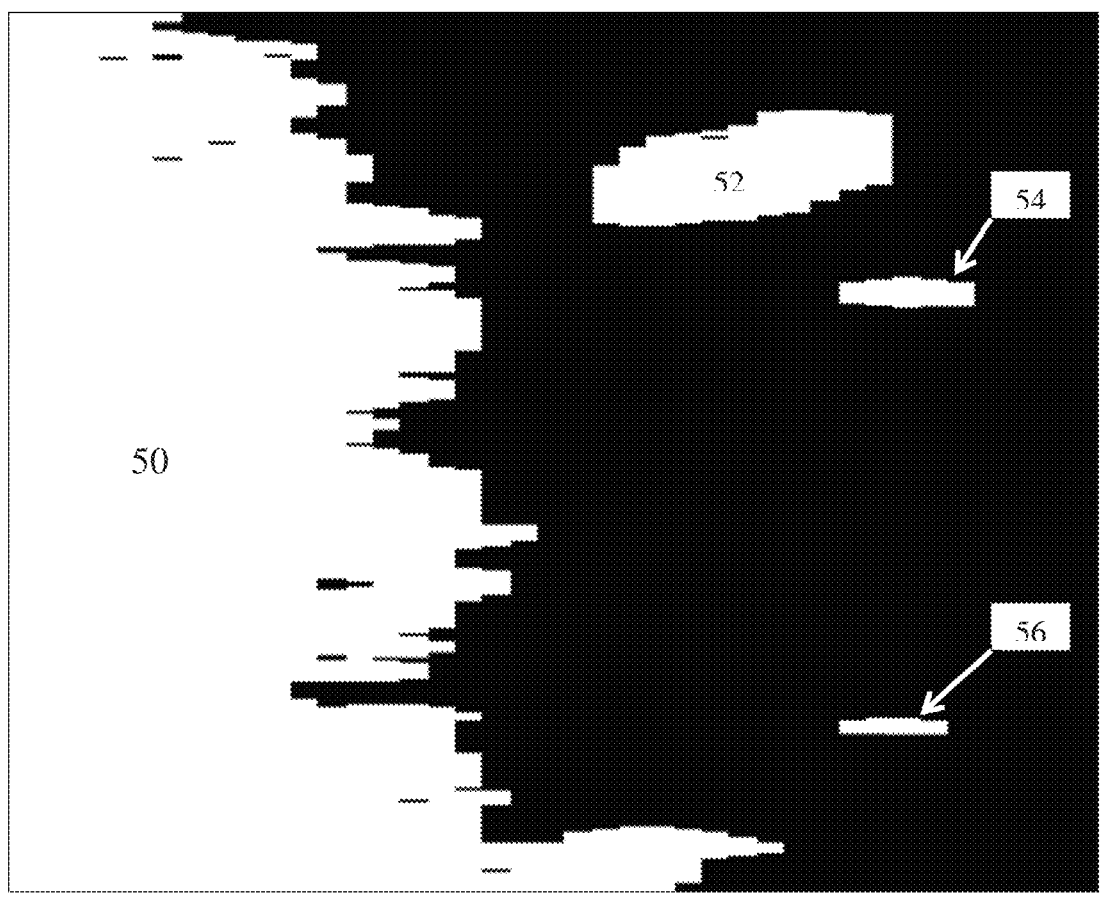
FIG. 3 is the example image derived from the data for FIG. 2 segmented to identify separate, contiguous regions of motion.

FIG. 3 shows one example of segmenting using the region of interest of the FIG. 2 example. Within the region of interest, after spatial filtering, four contiguous regions 50-56 of flow are found. The two larger of the regions are labeled as 50 and 52. The largest region 50 of connected flow locations results from the combination of several regions in FIG. 2 due to the low pass filtering.

In the example of FIG. 3, the largest region 50 appears to be, at least in part, due to flash artifact. The size and shape of the region correspond more with flash than with flow. The other regions 52-56 appear sized and shaped as is typical or expected for vessel flow within a patient, so may not be subject to flash artifact or may be subject to less flash artifact.

In act 36, each of the contiguous regions 50-56 is categorized as corresponding to flash or not. The likelihood of each of the contiguous regions including flash artifact is determined. The categorization is binary, such as yes or no. Alternatively, the categorization has three or more levels, representing a greater resolution in the likelihood that the region 50-56 is flash artifact.

The categorization is performed for each of the contiguous regions 50-56. The identification is repeated so that the likelihood is determined for each contiguous region separately and/or independently. The different contiguous regions of connected ones of the locations with Doppler values are assigned the same or different likelihood. For example, the region 50 may be assigned a greater likelihood. The categorization is repeated for each of regions 52-56, and those likelihoods may be the same, greater, or lesser than for others of the regions 50-56. In alternative embodiments, a high probability of flash in one contiguous region 50-56 is used to increase the likelihood of flash in another of the contiguous regions 50-56.

Any characteristics may be used to categorize. In one embodiment, a single characteristic is used. In other embodiments, two or more (e.g., three or four) characteristics are used. Where more than one characteristic is used, the likelihoods from the different characteristics or a mapping of the combination of characteristics to a likelihood is used. For example, each region is assigned conditional probabilities of being flash artifacts given multiple observations (e.g., size and shape). The conditional probabilities are combined to find the probability of flash for the contiguous region.

The characteristics are of the contiguous region. For example, the size, shape, and/or location of the contiguous region are used for categorizing. As another example, the characteristic is of the motion data of the contiguous region, such as a data statistics (e.g., spatial variance) of the motion data within the contiguous region. In one embodiment, the size and shape are used. In another embodiment, the size and shape with one or both of spatial variance, and location are used.

The region as segmented is used to calculate the characteristics. Alternatively, the region as segmented is used in a further process to calculate the characteristics, such as using the region from segmenting as a mask for the ultrasound data, and using motion locations or data within the mask but from prior to the segmenting.

For the size, the area or volume of the contiguous region is calculated. Each pixel, voxel, or scan sample location represents an area or volume. This area or volume is multiplied by the number of motion locations in the contiguous region to find the area or volume of the motion in the contiguous region. Other approaches for calculating area or volume may be used, such as approximating by fitting (e.g., rotating, translating, and/or scaling) a shape to the region and using the area or volume of the shape. Another approach may be to calculate the percentage of the region of interest occupied by the contiguous region as the size.

An indication of the likelihood of the contiguous region including flash artifact is assigned based on the size, such as based on the area or volume. Any linear or non-linear mapping of size to flash artifact probability may be used. In one embodiment, the mapping is programmed or found from empirical data or machine learning. Different size regions are associated with different likelihoods of including flash. In general, regions above a given size in a given application are more likely to be flash. Smaller or regions sized appropriate for the motion of tissue or flow in a scan region are less likely to be flash. For example in cardiac imaging away from the heart, regions whose physical size is larger than normally expected blood vessels are assigned higher probabilities.

For shape, a characteristic of the shape of the contiguous region is calculated. Any characteristic of shape may be used, such as type of shape (e.g., rectangular, circular, ellipsoid, or linear) or edge variance. In one approach, shapes associated with flash or shapes associated with motion regions are correlated with the contiguous shape. The amount of correlation or the shape with the greatest correlation to the contiguous shape is the characteristic. In another approach, a variance or standard deviation from a low pass filtered edge or smooth contour fitting to the contiguous region is calculated as the characteristic.

An indication of the likelihood of the contiguous region including flash artifact is assigned based on the shape, such as based on the level of correlation, correlated shape, level of edge smoothness, or other shape characteristic. Any linear or non-linear mapping of size to flash artifact probability may be used. In one embodiment, the mapping is programmed or found from empirical data or machine learning. Different shaped regions are associated with different likelihoods of including flash. Motion or flow regions are likely to have smoother edges, so a measure of variance or lack of smoothness may indicate whether the region is associated with flash. For example, the region 50 of FIG. 3 has edges with large variance, indicating more likely to be flash. The region 52 has edges with less variance, indicating less likely to be flash. Motion or flow regions are likely to be circular or ellipse shaped, so contiguous regions with narrower or more rectangular shapes may be more likely to be flash. Due to proximity of scanning time and/or position, the shape of flash artifacts correlates well with interleave groups of receive lines. Contiguous regions whose shape has a high resemblance to interleave group (e.g., pie or rectangular shape) are assigned a greater likelihood of flash artifact.

For signal statistics, a statistic of the color flow ultrasound data for the region is calculated. For example, the spatial variance or standard deviation is calculated. As another example, the mean is calculated. In yet another example, a measure of aliasing is calculated. Other statistics or a combination of statistics may be used. The statistic is of one or more types of data, such as a statistic for velocities, a statistic for energy, a statistic for variance of velocity, and/or statistics for combinations thereof.

An indication of the likelihood of the contiguous region including flash artifact is assigned based on the signal statistic or statistics for the contiguous region. Any mapping of statistic to probability may be used. Due to high correlation of flow values within the artifacts, a region that has a low spatial variance in flow parameters, such as velocity or energy, is assigned a higher probability of flash. Conversely, a contiguous region with greater variance is assigned a lower probability of flash.

For location, a distance of a center of mass to a center of a region of interest, shortest edge distance to a center of the region of interest, shortest distance to a edge of the region of interest, average distance of the edges of the contiguous region to the center or edges of the region of interest, or other measure of location of the contiguous region relative to the region of interest is calculated. An indication of the likelihood of the contiguous region including flash artifact is assigned based on the location. Users have the natural tendency to align the flow of interest with the center of the region of interest. Contiguous regions whose centers of mass are closer to the edges of the region of interest are assigned higher probabilities of flash artifact. A contiguous region with a center of mass close to or at the center of mass of the region of interest are assigned a lower probability.

Where more than one indication for a given contiguous region is provided, the indications may be combined. For example, an average probability is calculated. To account for different strengths of indication of flash for different characteristics, a weighted average may be used. For example, the size and shape are more likely indicative of flash than signal statistics and location. As a result, a weighted average is used. The likelihoods for size and shape are weighted more heavily in the weighted averaging than the likelihoods for location or signal statistics. Any weighting scheme may be used. In other embodiments, the combinations of indications are used in a look-up table or mapped to a final likelihood. For example, binary indications are used for each characteristic. Different combinations of positive and negative indications of flash are used to indicate the likelihood of flash.

The final probability or likelihood is a percentage. Alternatively, different levels or scales are used so that the probabilities, including the final probability are in reference to position along the scale (e.g., 10 is highest likelihood of flash and 1 the least likelihood of flash with numbers in between linearly or non-linearly mapping to other likelihoods of flash between the highest and lowest). Any relation of the categorization to flash may be used.

In act 40, the flash artifact is suppressed, at least partially. The suppression is in the color flow ultrasound or other motion data. The Doppler values or estimates are altered, such as reduced. The motion data is changed in response to identifying flash artifact. If the categorization results in a probability above a threshold amount, then the flash is suppressed. Rather than or in addition to using a threshold, different levels of suppression may be provided, such as more or less suppression for greater or lesser probability of flash. Linear or non-linear mapping of probability to amount of flash suppression (i.e., amount of reduction) may be used. For greater flash suppression, greater reduction or alteration in the motion values is provided.

For velocity values, the reduction is moving the velocity closer to zero. The negative or positive velocities are reduced to lower negative or positive velocities while maintaining the sign. For energy values, the estimates are not signed. The reduction is moving the estimates closer to zero.

The suppression is applied the same to the entire contiguous region. For example, all of the motion values are reduced by a same amount. Where the reduction is greater than the motion value, then the motion value is zeroed, so the amount of reduction may vary even where the same reduction is attempted to be applied to all of the motion values of the contiguous region. In other embodiments, the amount of reduction varies as a function of the motion value. For example, a reduction level is selected for the contiguous region. The percentage of the reduction level to apply depends on the motion value. Greater motion values may have greater percentage of the amount of reduction. As another example, the spatial variance determines the percentage. For locations associated with little spatial variance, all or more of the reduction is applied. For locations associated with greater spatial variance, less of the reduction is applied.

The amount of reduction is based on the categorization. The suppression is based on the size, shape, location, and/or signal statistics. Artifacts are suppressed by zeroing and/or reducing flow or motion values (such as power and/or velocity) by an amount based on the flow regions' respective probability of being flash.

In a further embodiment, the amount of reduction is based on the categorization and one or more local statistics of motion values. For example, an amount based on categorization is selected. The amount is then scaled based on the mean energy and/or velocity. As another example, the mean is calculated. The reduction is selected as a percentage of the mean where the percentage is mapped from the categorization or probability.

A combination of categorization and local statistics may be used. For example, a contiguous region with very high probability is completely removed regardless of local statistics, whereas areas with lower probability have their flow power reduced proportionally to the local statistics and the probability of being flash. In an alternative to changing power, velocity values are reduced based on the mean and/or standard deviation of the identified region. The areas with very low probabilities are left intact or not altered.

Different contiguous regions are altered the same or differently. Since different probabilities and/or local statistics may be provided for the different contiguous regions, different amounts of reduction may be provided for the different contiguous regions. For example, the region 50 has a higher probability of being flash, so a 75% reduction is applied. The region 52 has a lower probability of being flash, so a 25% reduction is applied. The regions 54 and 56 have the lowest probability (e.g., no probability or probability below a threshold) of being flash, so no reduction is applied. The reduction for any two or more contiguous regions may be the same. Factoring in the local statistics may cause greater variability between regions for the amount of reduction. Consequently, flash artifacts of various shapes and strength may be substantially removed or subdued while weak blood flow away from flash artifacts are minimally affected.

The reduction may result in some locations having zeroed out motion (e.g., velocity and/or energy). If energy or velocity is zeroed, then both are zeroed. As a result, some locations that indicate motion as acquired no longer show motion, so B-mode information or no motion information is provided for that location.

In act 42, a color flow (e.g., Doppler energy or Doppler velocity), Doppler tissue motion, or other motion image is generated. The motion data after the suppression of the artifact is used to create a color or motion image. For suppression of velocities or other color flow data prior to color mapping, the altered color flow data is mapped to the display values. For suppression of the velocities or other color flow data as mapped to colors, the altered colors are used as the display values. The image includes motion values (e.g., velocities or energy) that have been altered to remove or reduce the flash artifact. Fewer of the pixels are mapped to the high or highest range of colors as compared to mapping without the suppression alteration. Some pixels may no longer be associated with motion due to zeroing or reducing to or below a noise level.

The image may include other information. For example, the image is an overlay of the color flow data with B-mode data. For non-tissue locations or locations associated with sufficient flow, the color flow data (e.g., velocities) are used to determine a color to display. For tissue locations or low/no flow locations, the B-mode data is used.

Figure 4:
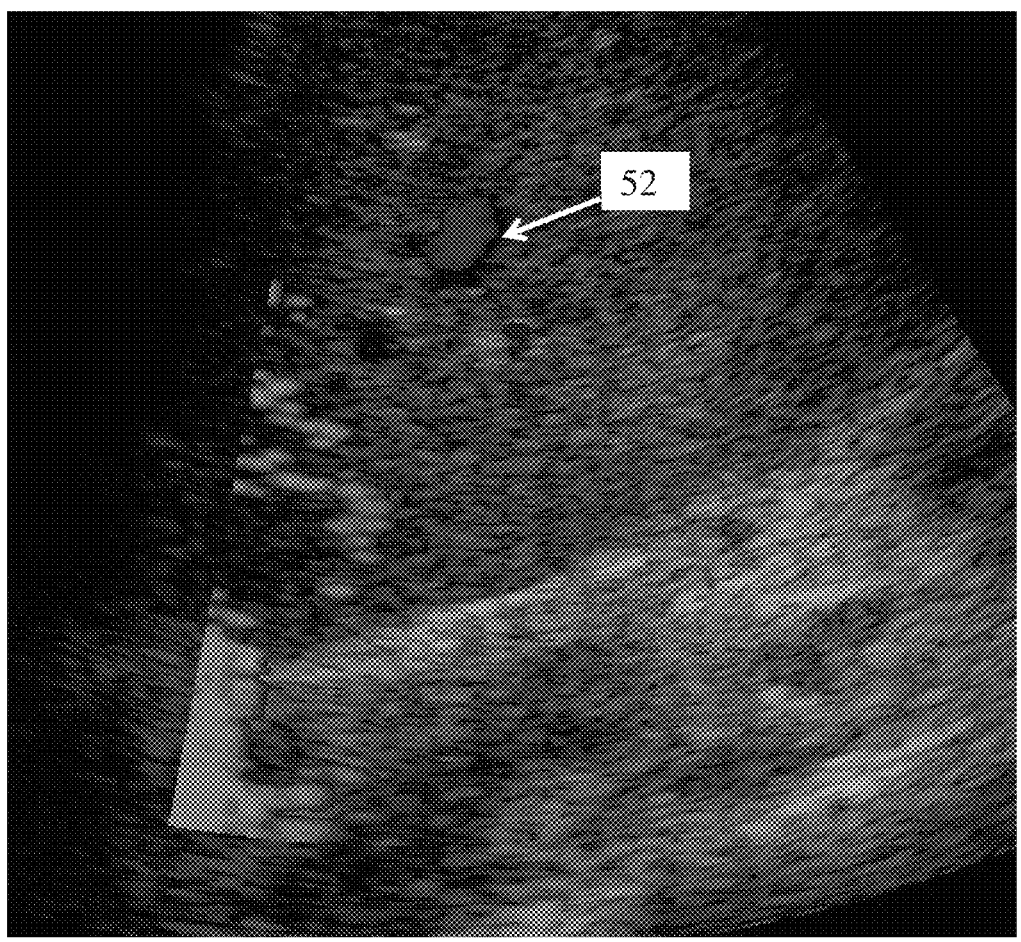
FIG. 4 is an example of the image of FIG. 2 with flash suppressed.

FIG. 4 shows an example color flow image of velocities generated with suppression. The image is the same as FIG. 2, but with the velocities suppressed for flash artifact. The region 52 is changed little or not at all. The region 50 has a greater suppression, so many locations are no longer associated with flow. B-mode data is displayed instead. Other locations show flow, but at lesser velocities than in FIG. 2. The suppression results in the flow regions looking less like flash and more like expected flow regions.

Relative terminology, such as associated with amounts of altering or with probabilities, indicates a difference between values. For example, lower and higher alterations are magnitudes with relative difference, rather than absolutes. Different imaging situations may have different values, based on experimentation, dynamic range, imaging system, and/or user preference. The actual values may be any value.

FIG. 3 shows one embodiment of a system 10 for flash suppression in color flow, tissue motion, or other motion imaging. The system 10 includes a transmit beamformer 12, a transducer 14, a receive beamformer 16, a memory 18, a filter 20, a flow estimator 22, a memory 28, a processor 24, and a display 27. Additional, different or fewer components may be provided. For example, the system includes a B-mode detector. As another example, the flow estimator 22 and processor 24 are provided without the front-end components, such as the transmit and receive beamformers 12, 16. In one embodiment, the system 10 is a medical diagnostic ultrasound system. In an alternative embodiment, the system 10 is a computer or workstation. In yet another embodiment, the flow estimator 22 is part of a medical diagnostic ultrasound system or other medical imaging system, and the processor 24 is part of a separate workstation or remote system, making of the ultrasound imaging system.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, a wobbler array, combinations thereof, or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit and receive beamformers 12, 16 are a beamformer for scanning with the transducer 14. The transmit beamformer 12, using the transducer 14, transmits one or more beams to scan a region. Vector®, sector, linear or other scan formats may be used. The receive lines and/or transmit beams are distributed in the scan region. The receive beamformer 16 samples the receive beams at different depths. Sampling the same location at different times obtains a sequence for flow estimation.

In one embodiment, the transmit beamformer 12 is a processor, delay, filter, waveform generator, memory, phase rotator, digital-to-analog converter, amplifier, combinations thereof or any other now known or later developed transmit beamformer components. In one embodiment, the transmit beamformer 12 digitally generates envelope samples. Using filtering, delays, phase rotation, digital-to-analog conversion and amplification, the desired transmit waveform is generated. Other waveform generators may be used, such as switching pulsers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal or other waveforms of a desired center frequency or frequency band with one, multiple or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and/or combinations thereof. A transmit beam focus is generated based on these beamforming parameters.

The receive beamformer 16 is a preamplifier, filter, phase rotator, delay, summer, base band filter, processor, buffers, memory, combinations thereof or other now known or later developed receive beamformer components. The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. In one embodiment, the beamform summer is configured to sum in-phase and quadrature channel data in a complex manner such that phase information is maintained for the formed beam. Alternatively, the beamform summer sums data amplitudes or intensities without maintaining the phase information.

The receive beamformer 16 is operable to form receive beams in response to the transmit beams. For example, the receive beamformer 16 receives one, two, or more receive beams in response to each transmit beam. The receive beams are collinear, parallel and offset or nonparallel with the corresponding transmit beams. The receive beamformer 16 outputs spatial samples representing different spatial locations of a scanned region. Once the channel data is beamformed or otherwise combined to represent spatial locations along the scan lines 11, the data is converted from the channel domain to the image data domain. The phase rotators, delays, and/or summers may be repeated for parallel receive beamformation. One or more of the parallel receive beamformers may share parts of channels, such as sharing initial amplification.

For imaging motion, such as tissue motion or fluid velocity, multiple transmissions and corresponding receptions are performed for each of a plurality of substantially same spatial locations. Phase changes between the different receive events for each given location indicate the velocity of the tissue or fluid. A velocity sample group corresponds to multiple transmissions for each of a plurality of scan lines 11. The number of times a substantially same spatial location, such as a scan line 11, is scanned within a velocity sample group is the velocity sample count. The transmissions for different scan lines 11, different velocity sample groupings or different types of imaging may be interleaved. The amount of time between transmissions to a substantially same scan line 11 within the velocity sample count is the pulse repetition interval or pulse repetition frequency. Pulse repetition interval is used herein, but includes the pulse repetition frequency.

The memory 18 is video random access memory, random access memory, removable media (e.g. diskette or compact disc), hard drive, database, corner turning memory or other memory device for storing data or video information. In one embodiment, the memory 18 is a corner turning memory of a motion parameter estimation path. The memory 18 is configured to store signals responsive to multiple transmissions along a substantially same scan line. The memory 22 is configured to store ultrasound data formatted in an acoustic grid, a Cartesian grid, both a Cartesian coordinate grid and an acoustic grid, or ultrasound data representing a volume in a 3D grid.

The filter 20 is a clutter filter, finite impulse response filter, infinite impulse response filter, analog filter, digital filter, combinations thereof or other now known or later developed filter. In one embodiment, the filter 20 includes a mixer to shift signals to baseband and a programmable low pass filter response for removing or minimizing information at frequencies away from the baseband. In other embodiments, the filter 20 is a low pass, high pass or band pass filter. The filter 20 isolates velocity information from slower moving tissue and reduces velocities from fluids or alternatively reduces the influence of data from tissue while maintaining velocity information from fluids. The filter 20 has a set response or may be programmed, such as altering operation as a function of signal feedback or other adaptive process. In yet another embodiment, the memory 18 and/or the filter 20 are part of the flow estimator 22.

The flow estimator 22 is a Doppler processor or cross-correlation processor for estimating the color flow data. In alternative embodiments, another device now known or later developed for estimating velocity, power (e.g., energy), and/or variance from any or various input data may be provided. The flow estimator 22 receives a plurality of signals associated with a substantially same location at different times and estimates a Doppler shift frequency, based on a change or an average change in phase between consecutive signals from the same location. Velocity is calculated from the Doppler shift frequency. Alternatively, the Doppler shift frequency is used as a velocity. The power and variance may also be calculated.

Color flow data (e.g., velocity, power, and/or variance) is estimated for spatial locations in the scan region from the beamformed scan samples. For example, the flow data represents a plurality of different locations in a plane.

The flow estimator 22 may apply one or more thresholds to identify sufficient motion information. For example, velocity and/or power thresholding for identifying velocities is used. In alternative embodiments, a separate processor or filter applies thresholds. In other embodiments, the thresholding is applied after any motions suppression, such as by the processor 24.

The flow estimator 22 outputs frames of data representing the scan region at different times. The beamformed samples for a given flow sample count are used to estimate for a time. A moving window with overlap of the data is used to estimate for other times. Velocities for each location at different times are output.

The processor 24 is a digital signal processor, a general processor, an application specific integrated circuit, field programmable gate array, control processor, digital circuitry, analog circuitry, graphics processing unit, combinations thereof or other now known or later developed device for implementing calculations, algorithms, programming or other functions. The processor 24 operates pursuant to instruction provided in the memory 28, or a different memory for flash artifact suppression in medical diagnostic ultrasound.

The processor 24 receives color flow data from the flow estimator 22, the memory 28, and/or another source. In one embodiment, the processor 24 implements one or more of the algorithms, acts, steps, functions, methods or processes discussed herein, by processing the data and/or controlling operation of other components of the system 10. Additional or multiple processors may be used to implement various aspects of the algorithms.

The processor 24 is configured by software and/or hardware to identify and suppress flash artifacts in the motion values. Flash artifact is identified separately for each of any number of unconnected regions of motion within a scan region. The processor 24 segments the unconnected regions of motion as separate regions with contiguous motion. Separate regions of connected or adjacent locations of motion are found, such as by the processor 24 applying low pass spatial filtering and boundary or edge detection. Where a given location of flow is immediately adjacent another location of flow, such as in any of four or eight directions, the locations are joined into a same grouping. The process continues to group the locations that are connected or adjacent and to identify separate groups of the connected locations. The separate groups are not connected together, such as having non-motion locations separating the closest locations to each other.

The processor 24 is configured to identify the flash artifact as a function of one or more characteristics of a given unconnected region. The identification of flash is performed separately for each unconnected region. Any characteristics may be used, such as the size and shape with or without (1) location in the region of interest of the unconnected region and/or (2) motion data statistic of the unconnected region. Using the characteristics, the level or likelihood of flash in each unconnected region is determined.

The processor 24 is configured to reduce the motion values by different amounts for the unconnected regions. The amount of reduction is based on the level or likelihood of flash for the corresponding unconnected region. One or more statistical values for the motion data in the unconnected region may be used with the level or likelihood of flash to determine the amount of reduction.

The processor 24 is configured to generate a motion image, such as a color flow or Doppler tissue motion image. The image is generated with artifact suppressed motion values. The processor 24 passes a frame of data for motion mapping to display values or maps and passes the display values. The motion values are further scan converted or the processor 24 operates on scan converted motion values.

The memory 28 is video random access memory, random access memory, removable media (e.g. diskette or compact disc), hard drive, database, or other memory device for storing color flow or other motion data. The stored data is in a polar or Cartesian coordinate format. The memory 28 is used by the processor 24 for the various filtering, detecting, identifying, spatial filtering, suppressing, calculating, or other acts described for FIG. 1.

The instructions for implementing the processes, methods and/or techniques discussed above are provided on computer-readable storage media or memories, such as a cache, buffer, RAM, removable media, hard drive or other computer readable storage media, such as represented by the memory 28. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 27 is a CRT, LCD, plasma, projector, monitor, printer, touch screen, or other now known or later developed display device. The display 27 receives RGB, other color values, or other motion values and outputs an image. The image may be a gray scale or color image. The image represents the region of the patient scanned by the beamformer and transducer 14, but with flash artifact suppression to account for undesired organ, transducer, and/or patient motion.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for flash suppression in color flow, the method comprising:

acquiring with ultrasound, using an ultrasound transducer of a diagnostic ultrasound system, color flow ultrasound data representing a patient, at least some of the color flow ultrasound data including a flash artifact due to organ motion, transducer motion, or patient motion in the acquiring;

segmenting, by a processor of the diagnostic ultrasound imaging system, the color flow ultrasound data into one or more contiguous regions of flow, each of the one or more contiguous regions being unconnected to others of the one or more contiguous regions;

calculating, by the processor of the diagnostic ultrasound imaging system, a size characteristic of each of the one or more contiguous regions;

calculating, by the processor of the diagnostic ultrasound imaging system, a shape characteristic of each of the one or more contiguous regions;

categorizing, by the processor of the diagnostic ultrasound imaging system, each of the one or more contiguous regions as flash artifact or not flash artifact by the size characteristic and the shape characteristic of the one or more contiguous region, where categorizing comprises assigning a likelihood for each of the respective contiguous regions including the flash artifact from a combination of a probability from the size characteristic and a probability from the shape characteristic for the respective contiguous region;

suppressing, by the processor of the diagnostic ultrasound imaging system, any of the flash artifact in the color flow ultrasound data of each of the one or more contiguous regions based on the categorization for the respective contiguous region, the flash artifact resulting from the acquiring of the color flow ultrasound data with the ultrasound by the diagnostic ultrasound system; and generating on a display an ultrasound color flow image with the color flow ultrasound data resulting from the suppressing, the ultrasound color flow image representing blood flow within the patient with the flash artifact suppressed from the suppressing.

2. The method of claim 1 wherein acquiring comprises acquiring the color flow ultrasound data as velocity, power, variance, or combinations thereof.

3. The method of claim 1 wherein acquiring comprises scanning the patient with ultrasound and estimating from Doppler shifts.

4. The method of claim 1 wherein segmenting comprises low pass spatial filtering the color flow ultrasound data and detecting boundaries of the one or more contiguous regions from results of the low pass spatial filtering.

5. The method of claim 1 wherein segmenting comprises identifying groupings of connected flow locations that are unconnected with others of the groupings.

6. The method of claim 1 wherein calculating the size characteristic comprises calculating area of each of the respective contiguous regions; and
wherein categorizing comprises assigning indications of likelihoods of the respective contiguous regions including the flash artifact based on the respective areas.

7. The method of claim 1 wherein calculating the shape characteristic comprises calculating a boundary characteristic of the shape for each of the one or more contiguous regions; and
wherein categorizing comprises assigning an indication of likelihood of each of the respective contiguous regions including the flash artifact based on the boundary characteristic.

8. The method of claim 1 wherein categorizing further comprises categorizing as a function of spatial variance of the color flow ultrasound data in each of the one or more contiguous regions, and wherein suppressing comprises suppressing based on the size characteristic, shape characteristic, and spatial variance.

9. The method of claim 1 wherein categorizing further comprises categorizing as a function of location of each of the one or more contiguous regions relative to a flow region of interest, and wherein suppressing comprises suppressing based on the size characteristic, shape characteristic, and location.

10. The method of claim 1 wherein categorizing comprises determining the likelihood of each of the respective contiguous regions including the flash artifact from a weighted average of the probability from the size characteristic and the probability from the shape characteristic.

11. The method of claim 1 wherein suppressing comprises reducing values of the color flow ultrasound data by an amount based on the categorization.

12. The method of claim 1 wherein suppressing comprises zeroing some of the color flow ultrasound data, and wherein generating the color flow image comprises generating a velocity image with fewer locations of color flow information due to the zeroing.

13. The method of claim 1 wherein suppressing comprises reducing values of the color flow ultrasound data for one of the one or more contiguous regions less than for another of the one or more contiguous regions.

14. A non-transitory computer readable storage medium having stored therein data representing instructions executable by a programmed processor for flash artifact suppression in Doppler imaging, the storage medium comprising instructions for:
scanning, by a transducer and beamformer of an ultrasound system, a plurality of locations with ultrasound;
estimating, by a flow estimator of the ultrasound system, Doppler values for the locations, the Doppler values including the flash artifact due to organ, transducer, or patient motion in the scanning with ultrasound;
segmenting a group of spatially connected ones of the locations of the Doppler values;
calculating, by a processor of the ultrasound system, a size of the group of the spatially connected ones of the locations with the Doppler values as segmented;
calculating, by the processor of the ultrasound system, a shape of the group of the spatially connected ones of the locations with the Doppler values as segmented;
identifying, by a processor of the ultrasound system, the flash artifact being in the Doppler values of the group, the identifying being a categorization of the spatially connected locations as the group, the categorization of the group being a combination of a probability of flash from the calculated size and a probability of flash from the calculated shape of the group of spatially connected ones of the locations with Doppler values;
altering, by a processor of the ultrasound system, the Doppler values for the group of spatially connected ones of the locations in response to the identifying of the flash artifact, the altering reducing but not zeroing at least one of the Doppler values; and
generating, on a display of the ultrasound system, a Doppler image with the Doppler values, including altered Doppler values resulting from the altering.

15. A non-transitory computer readable storage medium having stored therein data representing instructions executable by a programmed processor for flash artifact suppression in Doppler imaging, the storage medium comprising instructions for:
scanning, by a transducer and beamformer of an ultrasound system, a plurality of locations with ultrasound;
estimating, by a flow estimator of the ultrasound system, Doppler values for the locations, the Doppler values including the flash artifact due to organ, transducer, or patient motion in the scanning with ultrasound;
calculating, by a processor of the ultrasound system, a size of a group of spatially connected ones of the locations with Doppler values;
calculating, by the processor of the ultrasound system, a shape of the group of spatially connected ones of the locations with Doppler values;
identifying, by a processor of the ultrasound system, the flash artifact being in the Doppler values of the group, the identifying being a categorization as a function of the calculated size and the calculated shape of the group of spatially connected ones of the locations with Doppler values;
altering, by a processor of the ultrasound system, the Doppler values for the group of spatially connected ones of the locations in response to the identifying of the flash artifact, the altering reducing but not zeroing at least one of the Doppler values; and
generating, on a display of the ultrasound system, a Doppler image with the Doppler values, including altered Doppler values resulting from the altering;
wherein identifying and altering are repeated for another group of spatially connected ones of the locations with Doppler values, the other group being spatially disconnected with the one group, the altering for the one group being by a different amount than the altering for the other group, and wherein generating comprises generating the Doppler image with the altered Doppler values for the one group and altered Doppler values for the other group.

16. The non-transitory computer readable storage medium of claim 14 wherein identifying comprises identifying as a function of the size, the shape, and a spatial variance of the Doppler values of the group.

17. The non-transitory computer readable storage medium of claim 14 wherein identifying comprises identifying as a function of the size, the shape, and a location in a region of interest of the locations of the group.

* * * * *